(12) United States Patent
Troadec et al.

(10) Patent No.: US 10,816,488 B2
(45) Date of Patent: Oct. 27, 2020

(54) PROCESS FOR CALIBRATING A SENSOR, AUTOMATED METHOD FOR ONLINE MONITORING OF THE CHANGES TO A LIQUID BODY AND ASSOCIATED SENSOR

(71) Applicant: Wika Tech S.A.S., Le Bourget-du-Lac (FR)

(72) Inventors: Yann Troadec, Grenoble (FR); Raphaël Juston, Barraux (FR); François Chaudoreille, Gresy sur Aix (FR)

(73) Assignee: Wika Tech S.A.S., Le Bourget-du-Lac (FR)

( * ) Notice: Subject to any disclaimer, the term of this patent is extended or adjusted under 35 U.S.C. 154(b) by 60 days.

(21) Appl. No.: 16/306,629

(22) PCT Filed: Jun. 2, 2017

(86) PCT No.: PCT/EP2017/063534
§ 371 (c)(1),
(2) Date: Dec. 3, 2018

(87) PCT Pub. No.: WO2017/207790
PCT Pub. Date: Dec. 7, 2017

(65) Prior Publication Data
US 2019/0227007 A1    Jul. 25, 2019

(30) Foreign Application Priority Data
Jun. 2, 2016    (FR) .................................... 16 55024

(51) Int. Cl.
*G01N 23/223* (2006.01)
*G01N 33/28* (2006.01)
*G01N 33/30* (2006.01)

(52) U.S. Cl.
CPC ....... *G01N 23/223* (2013.01); *G01N 33/2858* (2013.01); *G01N 33/2888* (2013.01); *G01N 33/30* (2013.01)

(58) Field of Classification Search
CPC ............. G01N 23/223; G01N 33/2858; G01N 33/2888
See application file for complete search history.

(56) References Cited

U.S. PATENT DOCUMENTS

| 5,982,847 A * | 11/1999 | Nelson ............... G01N 33/2858 378/45 |
| 2002/0176536 A1* | 11/2002 | Ayukawa ............. G01N 23/223 378/66 |

(Continued)

OTHER PUBLICATIONS

PCT Application No. PCT/EP2017/063534, International Search Report, dated Jun. 30, 2017, 5 pages.

(Continued)

*Primary Examiner* — Taeho Jo
(74) *Attorney, Agent, or Firm* — Soquel Group LLC (57) ABSTRACT

A sensor for determining the overall content of a predetermined chemical element in a liquid body uses X-ray fluorescence technology and includes an X-ray source, an X-ray detector, and a cell intended to contain a sample of lubricant to be analyzed, and is provided with a wall forming a window for passage of X-rays, the wall of the sensor cell being produced from polyethylene terephthalate, the cell also including a casing defining an internal volume for receiving the sample. A procedure for calibrating the sensor, and an automated method for online monitoring are also described and claimed.

15 Claims, 8 Drawing Sheets

(56) References Cited

U.S. PATENT DOCUMENTS

| | | | | |
|---|---|---|---|---|
| 2003/0058990 | A1* | 3/2003 | Kaiser | G01N 23/223 378/45 |
| 2005/0232391 | A1* | 10/2005 | Katz | G01N 23/223 378/45 |
| 2008/0310588 | A1* | 12/2008 | Cooper | G01N 23/223 378/45 |
| 2013/0170613 | A1* | 7/2013 | Utaka | G01N 23/223 378/46 |
| 2015/0355115 | A1* | 12/2015 | Mustafina | G01F 1/38 378/207 |
| 2016/0123910 | A1* | 5/2016 | Lee | G01N 33/20 378/48 |
| 2017/0108424 | A1* | 4/2017 | Yamada | G01N 23/223 |

OTHER PUBLICATIONS

Akiho et al., Speciation and oxidation reaction analysis of selenium in aqueous solution using X-ray absorption spectroscopy for management of trace element in FGD liquor, Fuel, Jul. 3, 2012, pp. 156-161, vol. 102.

Balaji et al., "Determination of uranium in process stream solutions from uranium extraction plant employing energy dispersive X-ray fluorescence spectrometry", Journal of Radioanalytical and Nuclear Chemistry, Oct. 21, 2011, pp. 371-376, vol. 294, No. 3.

Manning et al., "Rutile solubility in albite-H2O and Na2Si3O7—H2O at high temperatures and pressures by in-situ synchrotron radiation micro-XRF", Earth and Planetary Science Letters, pp. 730-737, Aug. 15, 2008, vol. 272, Nos. 3-4, North Holland Publ. Co., NL.

Núñez-Milland et al., "Quantification of phosphorus in single cells using synchrotron X-ray fluorescence", Journal of Synchrotron Radiation, pp. 560-566, Jul. 1, 2010, vol. 17, No. 4.

Rigaku, "Application package for X-ray fluorescence analysis—simple, fast calibration for quantitative analysis", Jan. 1, 2010. https://www.rigaku.com/downloads/journal/RJ26-2/RJ26-2_31-32.pdf.

* cited by examiner

PROCESS FOR CALIBRATING A SENSOR, AUTOMATED METHOD FOR ONLINE MONITORING OF THE CHANGES TO A LIQUID BODY AND ASSOCIATED SENSOR

CROSS-REFERENCE TO RELATED APPLICATIONS

This application claims benefit under 35 USC § 371 of PCT Application No. PCT/EP2017/063534 entitled PROCEDURE FOR CALIBRATING A SENSOR, AUTOMATED METHOD FOR ONLINE MONITORING OF THE CHANGES TO A LIQUID BODY AND ASSOCIATED SENSOR, filed on Jun. 2, 2017 by inventors Yann Troadec, Raphael Juston and François Chaudoreille. PCT Application No. PCT/EP2017/063534 claims priority of French Patent Application No. 16 55024, filed on Jun. 2, 2016.

FIELD OF THE INVENTION

The invention relates to a process for calibrating a sensor for determining the overall content, in a predetermined chemical element, of a liquid body. The invention also relates to an automated method for online monitoring of the changes to the overall content in a predetermined chemical element of a liquid body, which comprises implementing such a calibration process. Lastly, the invention relates to a sensor making it possible to implement this process and this method.

The invention relates to the field of measuring instruments for liquid bodies and associated services, in particular in the field of producing renewable energy, refining, land transport, chemistry and pharmacy.

BACKGROUND OF THE INVENTION

In the field of renewable energies, it is known that the situation of a piece of equipment should be monitored by analyzing a liquid circulating in said equipment. For example, it is known to monitor the composition of an oil lubricating a wind turbine. Such an analysis makes it possible to detect wear or corrosion phenomena that tend to occur in the transmission of a wind turbine. Maintenance operations are expensive, and currently, the inspection of the lubricant liquid of the wind turbines is done, after withdrawal, in a laboratory. Wind turbines are sensitive to wear or corrosion phenomena; their access difficulties require these analyses to be done on site, in particular to monitor the overall particulate iron content of the oil, this content resulting from abrasion phenomena. The overall iron content of the oil comprises the iron content present in the oil in particulate form, for example as iron oxide, and in dissolved form, for example in ionic form. This requires training staff and carrying elaborate equipment on site, the operation of which is relatively difficult to master, even by trained staff. Furthermore, this increases the crew's workload.

WO-A-2010/046591 provides for using an on-board system in which the oil leaving an engine is steered toward a functional component associated with a measuring system making it possible to determine its base number or its metal particle content. In practice, the oil flow rate leaving the engine is low, and the flow leaving the engine is made up of droplets that stream inside a pipe, to the point that it is not certain that the functional component is supplied with a sufficient oil flow rate for the measurements it performs to be accurate.

WO-A-03/091550 discloses a method for analyzing a liquid body in which a measurement, done using an XRF sensor on a sample of a liquid body to be inspected, is compared to measurements done on reference samples. This approach is provided for laboratory operations and requires a qualified workforce.

It is also known from U.S. Pat. No. 5,982,847 to use a spectrometer comprising an x-ray source and an x-ray detector associated with a cell made from a nonmetal or aluminum-based material, in which a lubricant circulates and which is equipped with a window transparent to x-rays. The spectrometer, which operates based on x-ray fluorescence technology, must be calibrated or benchmarked regularly, in order to avoid measuring errors.

Furthermore, laboratory equipment, like that known from U.S. Pat. No. 6,233,307, which could make it possible to detect the dissolved iron content of an oil for a wind turbine, is difficult to transport and complex to use, which makes it relatively impractical, even for roaming staff trained to that end. This type of equipment also must be calibrated regularly, which is complex to do.

Indeed, during the calibration of the known spectrometers, one or several control samples of liquid body are used on which measurements must be done, before the result of the measurement is compared to data stored in memory. Such an approach can be considered in the laboratory, but cannot be implemented in practice in an on-board installation, which is not provided for that purpose.

Similar problems arise for sensors for determining the content of a liquid body in another predetermined chemical element, in particular calcium, sulfur, vanadium, chromium, molybdenum, copper, silver, tin, aluminum, nickel, zinc, lead or phosphorus.

Similar problems also arise when one wishes to determine, reliably, the content of a predetermined chemical element in liquid bodies. For example, in the refining field, it may be timely to determine the content of heavy fuel treated with a given metal. This is why the present invention is applicable with different liquid bodies that may comprise one or several predetermined chemical elements.

SUMMARY OF THE DESCRIPTION

The invention more particularly aims to resolve these drawbacks by proposing a new process for calibrating a sensor for determining the content of a predetermined chemical element in a liquid body, said sensor using x-ray fluorescence technology and comprising an x-ray source, an x-ray detector and a cell intended to contain a sample of liquid body to be analyzed, said cell in turn including a casing that defines an internal volume for receiving the sample. According to the invention, this process comprises at least the following steps consisting of:
 a) establishing a first secondary x-ray spectrum comprising energy levels corresponding to the components of the material of the casing;
 b) operating the sensor while the internal volume of the casing does not contain a sample of the liquid body and establishing a second secondary x-ray spectrum;
 c) modifying the second spectrum, using the first spectrum as a base spectrum, for aligning the notable energy levels of the second spectrum on those of the first spectrum;
 d) recording the modified second spectrum as reference spectrum for the sensor.

The calibration process according to the invention therefore makes it possible to do without samples of liquid body to be analyzed and to do without introducing such samples into an installation that incorporates the sensor, using, as reference spectrum, a reference spectrum based on the components of the casing of the measuring cell of said sensor. The invention therefore does the complete opposite of the traditional calibration techniques, which consist of using representative samples of the product to be analyzed. Indeed, the process according to the invention bases the calibration on a material different from that which is analyzed, namely the material of the casing. The calibration process can therefore be implemented automatically, without having to place a sample of the liquid body in the cell of the sensor, or manually by a person without specific chemical skills, in particular a roaming agent responsible for maintaining wind turbines or a refining technician.

According to advantageous but optional aspects of the invention, such a process may incorporate one or more of the following features, considered in any technically allowable combination:

During step b), the internal volume of the casing exclusively contains a gas or a gaseous mixture, inert with respect to the x-rays, in particular air.

The casing is made from metal and the notable energy levels of the first reference spectrum comprise energy levels of metals making up the box.

The predetermined chemical element whereof one wishes to determine the content is iron and the metals whose energy levels make up the first spectrum do not comprise iron.

The first spectrum also comprises at least one energy level corresponding to the material of an anode of the x-ray source.

According to another aspect, the invention relates to an automated method for online monitoring of the changes in content of a predetermined chemical element of a liquid body circulating in a piece of equipment using an installation comprising a sensor for the content of a predetermined chemical element of said liquid body, said sensor using x-ray fluorescence technology and comprising an x-ray source, an x-ray detector and a cell intended to contain a sample of liquid body to be analyzed and including a casing defining an internal volume for receiving said sample. According to the invention, this method comprises a prior implementation of a process for calibrating the sensor, as considered above, as well as at least one series of steps consisting of determining, owing to the sensor previously calibrated, the content in predetermined chemical element of a sample of liquid body present or circulating in the internal volume of the casing.

According to other advantageous, but optional aspects of the invention, this method may incorporate one or more of the following features, considered in any technically allowable combination:

The predetermined chemical element is iron, or another chemical element, and the series of steps comprises detecting peaks for an energy level equal to about 6.4 keV and/or 7.06 keV in a secondary x-ray radiation spectrum emitted by the liquid body for iron, or specific rays for the other predetermined chemical element.

During the series of steps, a potential matrix effect is taken into account within the sample by applying a correction on the energy levels detected by the sensor, based on a predetermined interaction model between the components of the sample and/or the components of the casing.

If the effect of the matrix is taken into account, during the series of correction steps for the matrix effects, the calcium concentration of the sample is further taken into account by applying a correction on the energy levels detected by the sensor, based on a predetermined model.

The invention also relates to a sensor that in particular makes it possible to carry out the process and the method mentioned above, and more specifically, a sensor for using x-ray fluorescence technology to determine the overall content, in a predetermined chemical element, of a liquid body. This sensor comprises an x-ray source, an x-ray detector and a cell intended to contain a sample of the liquid body to be analyzed, this cell being equipped with a wall forming a window for the passage of the rays coming from the source or going toward the x-ray detector, this wall being made from polyethylene terephthalate.

Owing to this aspect of the invention, the sensor, which operates using x-ray fluorescence technology, allows a reliable measurement of the overall content of a predetermined chemical element in a liquid body. Within the meaning of the present invention, the overall content of a chemical element in a liquid body is the content of dissolved element, and in particular of said chemical element, in said liquid body. Advantageously, the sensor that uses the technology is a sensor of the iron content in the liquid body. The measurement performed is not significantly affected by the wall making up the passage window for the x-rays. Indeed, this wall, made from polyethylene terephthalate (PET), can be provided with a relatively insignificant thickness, in particular less than 200 μm (micrometers), while having satisfactory mechanical properties to withstand the pressure and vibration forces within a measuring installation. The component material of the wall also allows it not to be altered by the liquid body circulating in the cell.

According to advantageous, but optional aspects of the invention, the sensor may incorporate one or more of the following features, considered in any technically allowable combination:

The cell comprises a metal or metal alloy casing on which the wall is attached.

The cell comprises a hollow housing for receiving the wall and a threaded washer for immobilizing the wall in the hollow housing.

The membrane has a curved shape, with its concavity turned toward an inner volume of a housing of the cell.

The x-ray source, the x-ray detector and the cell are mounted on a common support.

A sighting axis of the x-ray source and a sighting axis of the x-ray detector form an angle of between 20 and 25°, preferably of about 22°.

The wall has a thickness of less than or equal to 200 μm, preferably less than or equal to 150 μm, still more preferably of about 125 μm. Alternatively, this thickness is less than or equal to 500 μm, preferably about 250 μm. Furthermore, this thickness is greater than or equal to 75 μm.

The sensor is compatible with a static or dynamic determination of the content of the liquid body in predetermined chemical element.

BRIEF DESCRIPTION OF THE DRAWINGS

The invention will be better understood and other advantages thereof will appear more clearly in light of the following description of two embodiments of an installation according to its principle, provided solely as an example and done in reference to the appended drawings, in which:

In FIGS. 8 to 11, the liquid body present or circulating in part of the installation is shown in gray.

DETAILED DESCRIPTION

The installation 2 shown in FIGS. 1 to 5 and 8 to 11 makes it possible automatically to monitor the changes to the overall iron content of a liquid body formed by a lubricant used in a piece of equipment, in the case at hand a machine M of the wind turbine type. A pipe 4 connects the piece of equipment M to a lubricant collection pan 6. In practice, the lubricant oil of the piece of equipment M flows in the pipe 4 with a pressure P4 of between 1.1 and 6 absolute bars. The oil flow rate of the pipe 4 can be low, to the point that the oil streams over the inner wall of this pipe.

Figure 1:
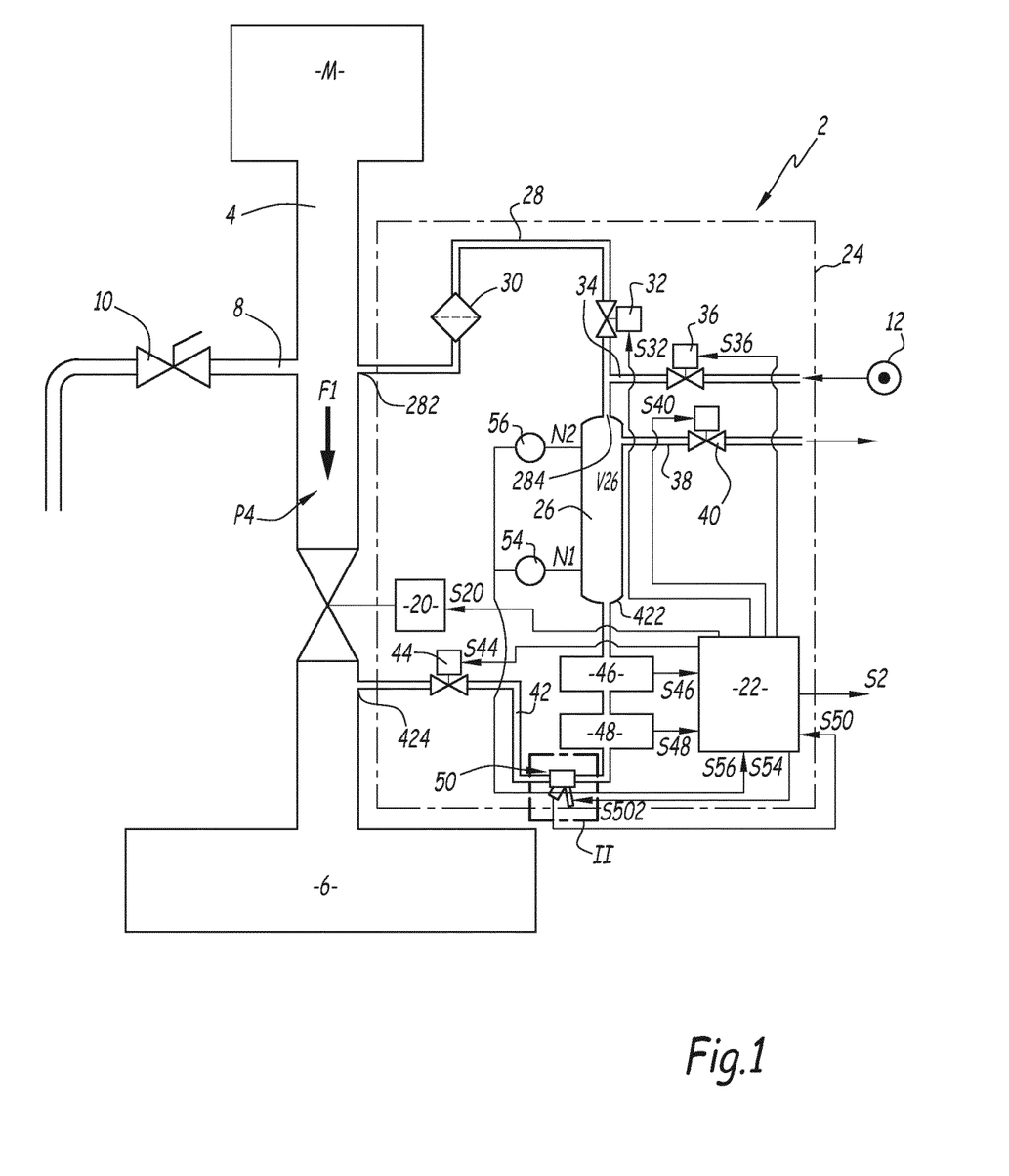
FIG. 1 is a schematic block diagram of an installation incorporating a sensor according to the invention.

A tapping 8 is provided on the pipe 4 and equipped with a valve 10 controlled manually, which makes it possible to withdraw a quantity of oil leaving the piece of equipment M in order to conduct physicochemical analyses, using an approach known in itself.

The installation 2 comprises a latch valve 20 mounted on the pipe 4 and that makes it possible to interrupt, selectively, the flow of oil in the pipe 4, toward the pan 6. The latch valve 20 is controlled by an electronic unit 22 using an electrical signal S20.

As shown only in FIG. 1, the installation 2 comprises a box 24, shown by its outline in axis lines and inside which the component elements of the installation 2 are placed, with the exception of the part of the latch valve 20 that is integrated into the pipe 4.

The installation 2 also comprises a buffer tank 26 that is positioned in the box 24 and is connected to the pipe 4 using a first bypass line 28.

Reference 282 denotes the mouth of the line 28. This mouth is positioned upstream from the valve 20 on the pipe 4. The first bypass line 28 is equipped, downstream from its mouth 282 toward its outlet 284 into the buffer tank 26, with a filter 30, a latch valve 32 and a tapping 34. The filter 30 is used to prevent overly large impurities from flowing in the first bypass line 28. The latch valve 32 makes it possible, as desired, to open or close the first bypass line 28. The valve 32 is controlled by the electronic unit 22, using an electrical signal S32. The tapping 34 is connected, through a controlled valve 36, to a pressurized air source 12 that is not part of the installation 2, but belongs to the standard equipment of a wind turbine.

In practice, the pressurized air source 12 can be a compressor in the wind turbine and that supplies a compressed air grid that is also used for pieces of equipment other than the installation 2. Alternatively, the source 12 can be a pump dedicated to the installation 2.

The installation 2 also comprises a tapping 38 connected to the tank 26, on which a latch valve 40 is mounted and that makes it possible to place the inner volume V26 of the tank 26 in communication with the ambient atmosphere.

In this embodiment, the tappings 34 and 38 are independent. Alternatively, they may be replaced by a single tapping, connected to the first line 28 or directly to the tank 26, on which the valves 36 and 40 are mounted in parallel, while respectively being connected to the pressurized air source 12 and the ambient atmosphere. In this case, it is possible to combine the valves 36 and 40 in the form of a single three-way valve.

The valves 36 and 40 are controlled by the electronic unit 22 using respective electrical signals S36 and S40.

The installation 2 also comprises a second discharge line 42 for discharging lubricant from the inner volume V26 of the tank 26 toward the pan 6. The second discharge line 42 is therefore positioned downstream from the first bypass line 28 and the tank 26, on the flow path of the lubricant. In the example, the second line 42 extends from the tank 26 toward the pipe 4. Its mouth 422 is situated in the lower part of the tank 26, while its outlet 424 is positioned on the pipe 4, downstream from the latch valve 20, as shown in the figures, which makes it possible to reduce the time of an analysis cycle, since the latch valve 20 can be closed to create an oil column in the pipe 4, while measuring steps take place. Alternatively, the outlet 424 of the second line 42 is positioned upstream from the latch valve 20, which makes it possible to carry out the emptying and unclogging steps of the filter 30 at the same time, and optionally to reduce the cost of the installation 2.

The second line 42 is equipped with a latch valve 44 that is controlled by the electronic unit 22 using an electrical signal S44.

Three sensors 46, 48 and 50 are positioned on the line 42, upstream from the valve 44.

The sensor 46 makes it possible to measure the density D, the viscosity V, the humidity H and the temperature T of a liquid body present or flowing in the second line 42, such as the lubricant oil leaving the piece of equipment M. The sensor may be of the type marketed by the company AVENISENSE under the name Cactus. Alternatively, the sensor 46 may be of another type or only make it possible to measure one or some of the aforementioned parameters.

The sensor 48 is a base number (BN), sometimes called alkalinity index, sensor. It may be a sensor working with infrared technology, in the infrared means, or any other sensor suitable for determining the BN of a lubricant.

The sensor 50 is a sensor for determining the overall iron content, i.e., the dissolved and/or particulate iron content, of a sample of liquid body, here lubricant, leaving the tank 26, using x-ray fluorescence technology.

As shown more particularly in FIGS. 2 to 5, the sensor 50 comprises an x-ray source 502, an x-ray detector 504 and a cell 506 that is mounted in series on the second line 42. To that end, the cell 506 is provided with an upstream coupling 506A that cooperates with the additional coupling element 42A provided on the line 42, as well as a downstream coupling element 506B that cooperates with a complementary coupling element 42B provided on the line 42.

Figure 2:
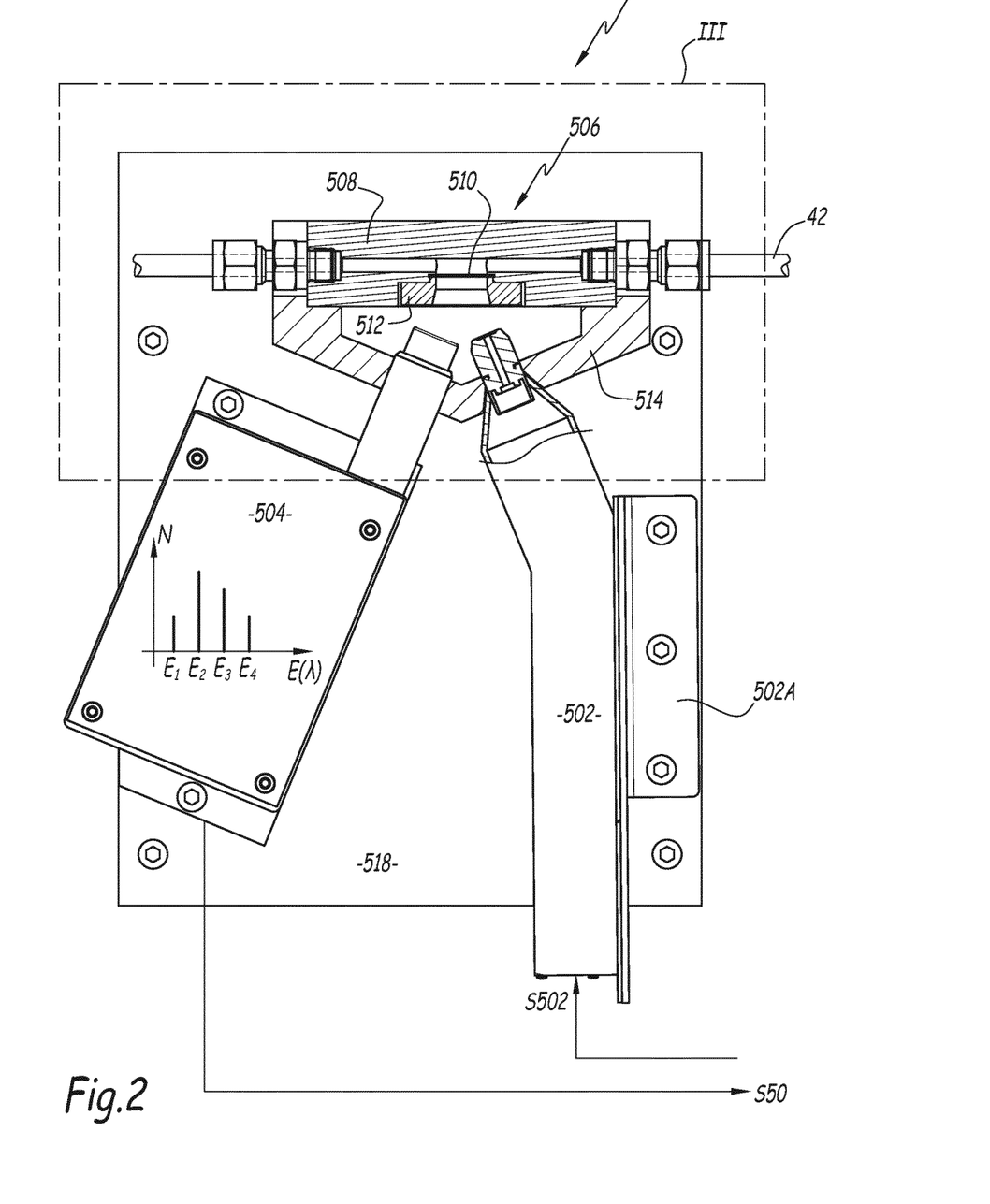
FIG. 2 is an enlarged view of detail II in FIG. 1, showing a sensor according to the invention for determining the content in a predetermined chemical element, in particular iron, used in the installation of FIG. 1.

The source 502 comprises a cathode and an anode between which electrons circulate, under the effect of a difference in potential of about 50 kV, a current of about 500 mA circulating in the cathode. The anode is made from metal, for example gold, tungsten, silver or rhodium. The power required for the source 502 is relatively modest, in particular between 4 and 10 W. A collimator 502C is used at the output of the source 502 in order to concentrate the electron beam centered on a sighting axis A502 of the source 502.

The rays emitted by the x-ray source are in the x-ray range, with a wavelength of between 0.01 and 10 nm, i.e., a frequency between about $3 \times 10^{19}$ and $3 \times 10^{16}$ Hz.

The detector 504 is of the SDD (Silicon Drift Detector) type, which comprises a single electrode on the front face, which collects the electrons generated by the interaction of the x-rays in the PN junction of a photodiode. This type of detector has the advantage of a low capacitance due to the small surface of its anode. This type of detector makes it possible to obtain a high counting rate, a good resolution and effective cooling by Peltier effect. Alternatively, the detector 504 is of the SI-PIN type, with a silicon photodiode, which has an intrinsic zone inserted between its two zones respectively positively and negatively doped.

The detector 504 is capable of counting the transmission "blows" at each energy level over a given period, which makes it possible to establish a spectrum of energy levels. Reference A504 denotes the sighting axis of the detector 504, which corresponds to the primary direction of the x-rays detected by said detector.

Figure 3:
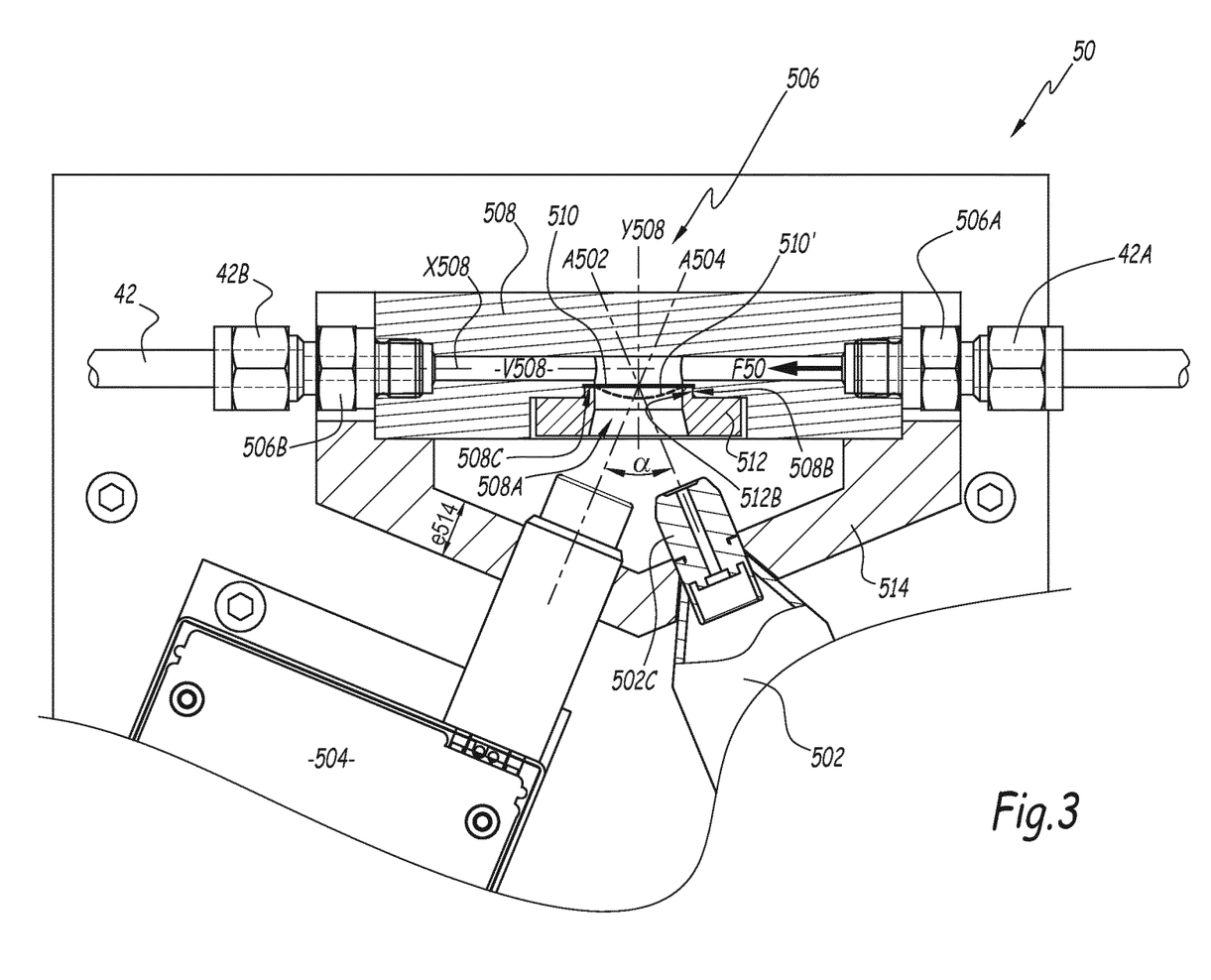
FIG. 3 is an enlarged view of detail III in FIG. 2.

The cell 506 comprises a body 508 made by machining or molding a block of metal. The body 508 is preferably made from aluminum or an aluminum-based alloy, for example Zicral (7075), which is an aluminum of alloy with zinc as primary alloy element. Alternatively, the casing 508 can be made from another aluminum-based alloy. Within the meaning of the present description, an aluminum-based alloy is an alloy that comprises at least 50 wt % aluminum. The use of an aluminum-based alloy allows the casing 508 to withstand the temperature, pressure and chemical composition of the lubricant flowing in the line 42. The absence or low proportion of iron contained in this alloy prevents the x-ray fluorescence of the overall iron content of the lubricant from being disrupted by the presence of a significant quantity of iron.

However, alternatively, it is possible to provide that the casing 508 is made from stainless steel.

The casing 508 defines a circulation volume V508 for the lubricant between the coupling elements 506A and 506B, in the direction of arrow F50 in FIG. 3. This volume V508 is tubular with a circular or rectangular section, as chosen by the designer of the casing 508. Reference X508 denotes a longitudinal axis of the volume V508. In practice, the volume V508 has a content level of between 1 and 5 ml. Thus, the use of the sensor 50 in the context of the present invention requires removing a relatively minimal quantity of oil in the pipe 4, which limits the disruptions in the operation of the machine M.

The casing 508 is provided with a piercing 508A, which is centered on an axis Y508 perpendicular to the axis X508 and which emerges in the volume V508. The piercing 508A has a circular section centered on the axis Y508 and provided with a tapping 508B.

The piercing 508A is closed by a disc-shaped wall 510, which may also be called "membrane" and which is kept bearing against the bottom of a spot facing 508C of the piercing 508A using a ring 512 provided with an outer thread 512B complementary to the tapping 508B and which cooperates with the latter. The wall or membrane 510 is mounted on the casing 508 by pressing it against the spot facing 508C, then screwing the ring 512 into the piercing 508A.

The ring 512 is made from the same metal or the same alloy as the body 508.

The wall 510 makes up a sighting window for the source 502 and for the detector 504 that allows the x-rays to go from the source 502 toward a lubricant sample contained in the volume V508 and from the volume 508 toward the detector 504.

The wall 510 is made from polyethylene terephthalate, or PET, which gives it satisfactory mechanical properties, whereas it may have a small thickness, less than or equal to 500 µm, preferably of about 250 or 125 µm, to the point that it does not disrupt the x-rays that come from the source 502 or that go toward the detector 504.

According to one embodiment, the thickness of the wall 510, which is measured perpendicular to the axis Y508, may be chosen to be less than 200 µm, preferably 150 µm, still more preferably around 125 µm. According to another embodiment, the thickness of the wall 510 may be chosen to be less than or equal to 500 µm, preferably around 250 µm. This thickness is greater than or equal to 75 µm, which gives the cell 506 good robustness.

According to one optional and advantageous aspect of the invention shown in dotted lines only in FIG. 3 with reference 510', the membrane 510 may have a curved shape, with its concavity turned toward the volume V508. In this case, the membrane is for example annealed at a temperature of between 40 and 70° C., preferably equal to about 60° C., for a period of between 30 and 60 mn, preferably equal to about 60 mn. This makes it possible to approach the glass transition of the PET making up the membrane 510 and to impart a satisfactory rigidity to said membrane, with the aforementioned curved shape.

This curved shape and/or this rigidity allow the membrane to withstand pressure variations within the volume V508. These pressure losses in particular result from head losses in the lines and supply tank of the sensor 50 and filling/emptying cycles of said volume. Thus, the membrane 510 can withstand a pressure of from 0 to 20 absolute bars, without risk of collapse of the membrane 510 toward the inside of the casing 508.

The source 502 and the detector 504 are mounted on a cover 514 that determines their position relative to the cell 506, more particularly relative to the casing 508 and the wall 510. This cover 504 surrounds the casing 508 on the side of the piercing 508A, such that it isolates the window formed by the wall 510 from the outside of the sensor 50. Reference e514 denotes the thickness of the cover 514. The material of said cover 514 and its thickness e514 are chosen such that they make up an effective shield against the x-rays that circulate between the source 502, the detector 504 and the cell 506. Said cell allows the free passage of the oil and makes it possible to perform static or dynamic oil analyses. In practice, the cover 514 can be made from stainless steel, for example of type 316, and the thickness e514 is chosen to be greater than 5 mm, preferably greater than 8 mm, still more preferably around 10 mm.

Furthermore, an additional shield 516 is mounted around the casing 508, on the side of said casing opposite the cover 514. For clarity of the drawing, said shield 516 is shown only in FIGS. 4 and 5.

Figure 4:
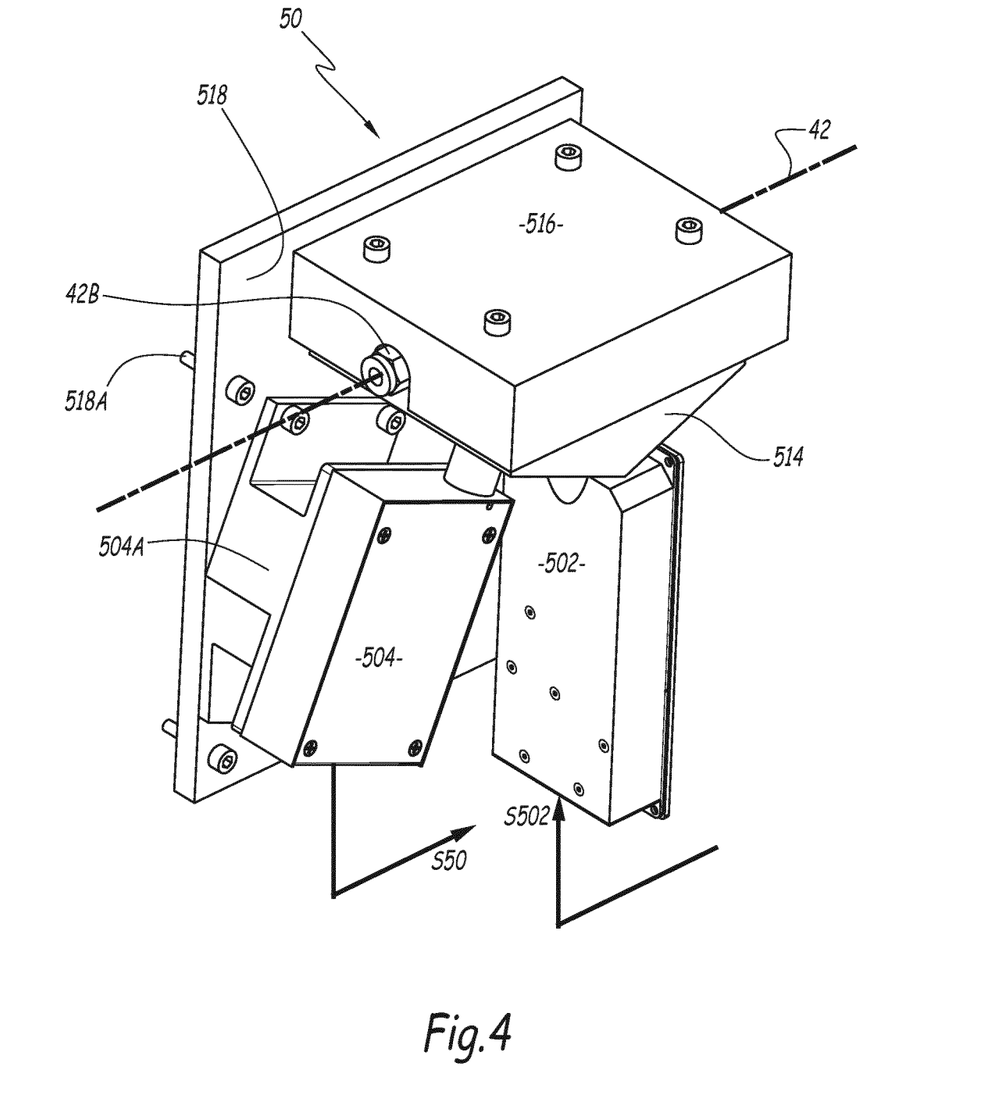
FIG. 4 is a perspective view of the sensor shown in FIGS. 2 and 3.
Figure 5:
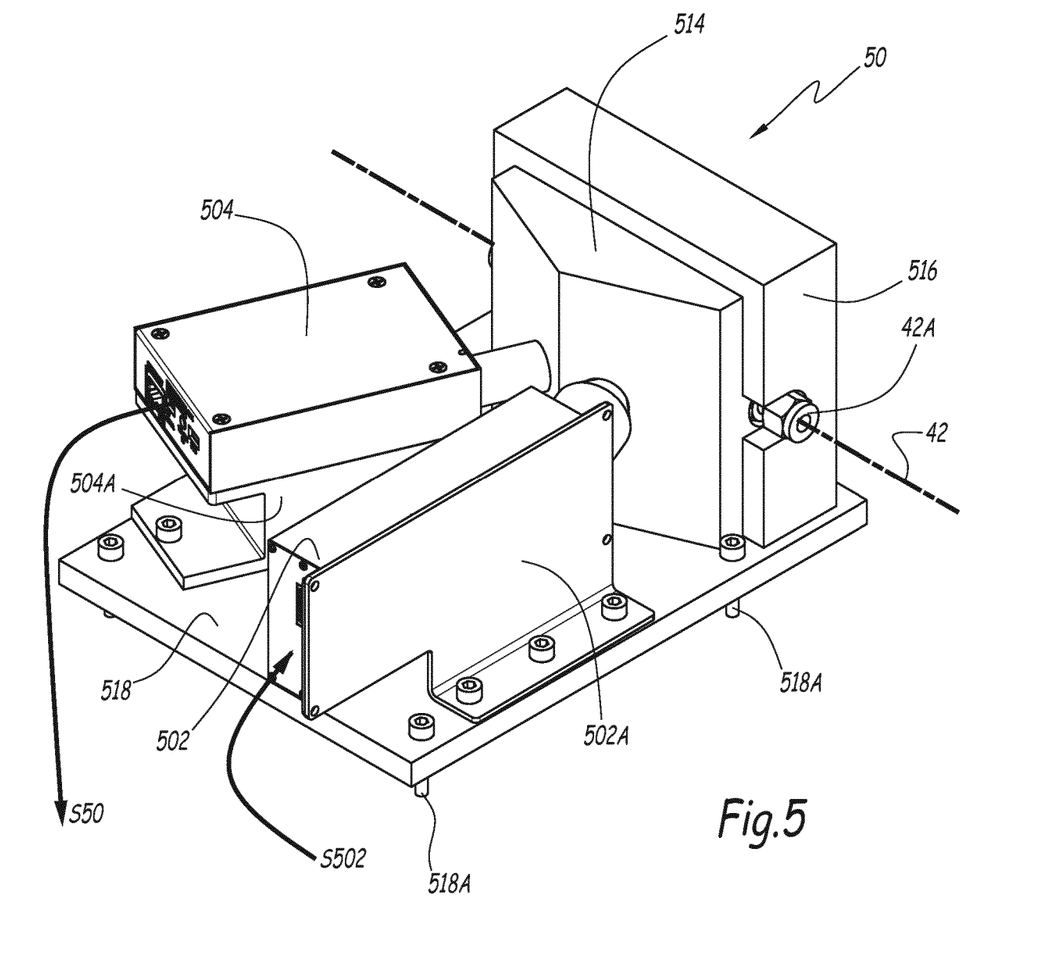
FIG. 5 is a perspective view, from another angle, of the sensor of FIGS. 2 to 4.

The parts 502, 504, 506, 514 and 516 of the sensor 50 are attached on a support 518 made up of a plate that can be immobilized in the box 24 using screws 518A. A bracket 502A and a spacer 54A are used respectively to attach the source 502 and the detector 504 on the support 518.

The fact that the parts 502, 504 and 506 are mounted on the support 518 imparts an industrial nature to the sensor 50 inasmuch as the latter can be handled in a unitary manner, in order to be incorporated into the installation 2 or during maintenance operations. This is much more practical than the case where the source 502 is a complex, bulky and expensive subassembly, of the synchrotron type, which is equipment limited to use in a laboratory.

In practice, the sensor 50 fits in an imaginary cube, the edge of which has a length equal to 500 mm, which makes it easier to place within the box 24.

Thus assembled, the sensor 50 makes up a subassembly that is easy to handle, and easily identifiable, which may be subject to a standard exchange operation by unscrewing the screws 518A and separating the coupling elements 506A and 42A, on the one hand, 506B and 42B, on the other hand.

The source 502 is commanded by the electronic unit 22 using a signal S502 and the detector 504 delivers, to the electronic unit 22, an output signal S50 from the sensor 50.

In practice, the axes X508, Y508, A502 and A504 are coplanar.

Reference α denotes an angle measured between the axes A502 and A504 outside the casing 508. The value of this angle α is between 20 and 25°, preferably around 22°.

During operation, the x-ray fluorescence technology of the sensor 50 is used to determine the overall iron content, i.e., the dissolved and/or particulate iron content, of a quantity of oil passing in the volume V508, at the outlet of the buffer tank 26. The measurement of the iron content is done by the sensor 50 when the lubricant flows in the second line 42, i.e., when the valve 44 is opened. This is then called dynamic measurement. Alternatively, this measurement can be done when the lubricant is static in the volume V508, i.e., when the valve 44 is closed. This is then called static measurement.

Whether the lubricant flows or is blocked in the body 508, the implementation of the sensor 50 involves the emission by the source 502 of an electron beam, in the x-ray range, which passes through the wall 510 and excites the atoms of a liquid located in the volume V508, in the case at hand a lubricant. The energy level of the x-rays from the source 502 is between 0 and 30 kilo electron volts (keV). To excite an iron atom and induce the layer change of an electron in said atom, it is necessary for the x-radiation entering the volume V508 to have an energy level greater than the characteristic energy level of the iron, or 6.4 keV.

In order to determine the dissolved or particulate iron content of a lubricant present in the volume V508, the detector 504 is adjusted to account for the rays induced with an energy level close to the characteristic energy levels of the iron, or equal to 6.4 keV and/or 7.06 keV, i.e., equal to 6.4 keV and/or 7.06 keV to within 5%.

In practice, the detector 504 is capable of counting, for each energy level, the number of "blows" corresponding to the emission of a photon by layer change of an electron at an atom. By incorporating the measurements done by the detector 504 over a predetermined period, for example equal to thirty seconds or one minute, it is therefore possible to establish a spectrum of the number N of blows detected over this period for each energy level E that corresponds to a wavelength λ characteristic of a chemical component. Such a spectrum S is shown schematically on the detector 504 in FIG. 2.

In order for the measurement done using the sensor 50 to be reliable, it is necessary for the spectrum S to in fact be representative regarding the energy levels $E_1$, $E_2$, $E_3$, $E_4$, etc. for which a peak is detected, i.e., in practice, regarding the position of the vertical bars of the spectrum S along the x-axis E, which is the axis of the energy levels.

Yet the intensity of the energy peaks can be affected by the transparency of the wall 510 as well as the wear of the electronic components belonging to the devices 502 and 504 or by the ambient temperature. Furthermore, the parameters of the radiation from the source 502 can change over time. It is therefore not possible to satisfy a unique calibration of the sensor 50 during its manufacture, i.e., at the beginning of its lifetime.

The calibration of the sensor 50 takes place by implementing a calibration process in which no sample of lubricant to be analyzed is used.

Figure 6:
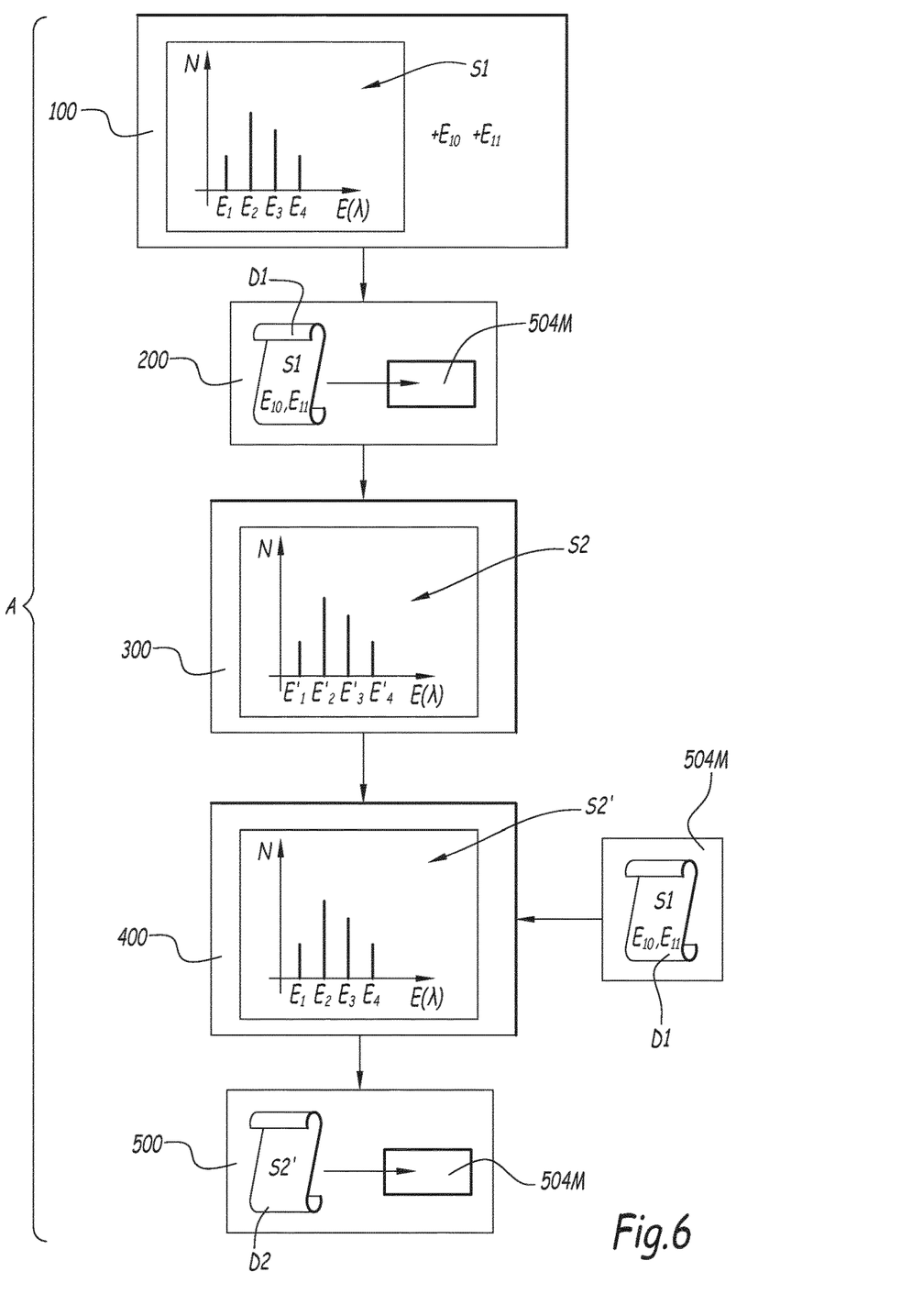
FIG. 6 is a block diagram of a calibration process according to the invention.

According to this process, during a first step 100 that may take place in the laboratory, a first secondary x-ray spectrum S1 is established comprising detection peaks for energy levels corresponding to the components of the material of the casing 508. In FIG. 6, four energy levels $E_1$, $E_2$, $E_3$ and $E_4$ are shown. In practice, depending on the composition of the material making up the casing 508, this number may be higher.

Preferably, if the material of the casing 508 is an aluminum-based alloy, the energy levels $E_1$, $E_2$, $E_3$, $E_4$, etc. correspond to metals other than iron.

After the first spectrum S1 has been established during step 100, the latter may be stored, in the form of a data set D1 and during step 200, in a memory 504M of the detector 504. Alternatively, the first data set D1 corresponding to the first spectrum S1 may be stored in a memory, not shown, of the electronic unit 22 of the installation 2.

Steps 100 and 200 are carried out only once for each sensor 50 during the manufacture of the sensor 50 if the data set is stored in the memory 504M, or during the manufacture of the installation 2 if it is stored in the memory of the unit 22.

If the component material of the casing 508 is determined for a series of sensors 50, step 100 can be carried out only once for all of these sensors, since the spectrum S1 is shared by said sensors.

During a subsequent step 300 of the calibration process, which may take place as many times as necessary during the lifetime of the sensor 50, the sensor 50 is operated, while the volume V508 is empty of lubricant. This volume V508 may be filled with a gas or a gaseous mixture inert to the x-rays, for example air. During this step 300, the sensor 504 establishes a second secondary x-ray spectrum S2.

If the sensor 50 is perfectly calibrated, the second spectrum S2 established in step 200 and the first spectrum S1 established in step 100 are identical, since they relate to the same material, namely that of the casing 508.

This is not necessarily the case, for the reasons considered above.

The calibration process of FIG. 6 therefore comprises an additional step 400 during which the second spectrum S2 is aligned on the first spectrum S1 by creating a second modified spectrum S2' that constitutes a corrected or improved version of the second spectrum S2, taking account of the first reference spectrum S1. If the two spectrums S1 and S2 are identical, step 400 takes place, but it has no effect on the spectrum S2.

Indeed, the notable energy levels $E'_1, E'_2, E'_3, E'_4, \ldots$ for which peaks are detected in the spectrum S2 may not be strictly equal to the notable energy levels $E_1, E_2, E_3, E_4, \ldots$ corresponding to the chemical components of the alloy making up the casing 508. Yet by comparing the heights of the peaks of the second spectrum S2 to those of the peaks of the first spectrum S1, it is possible to identify the peak of the spectrum S1 to which each peak of the spectrum S2 corresponds and to correct the values of the energy levels $E'_1, E'_2, E'_3, E'_4, \ldots$ corresponding to the peaks in order to arrange them, on the x-axis $E(\lambda)$ of the spectrum, in the same location as the notable energy levels $E_1, E_2, E_3, E_4$ of the first spectrum S1.

To that end, during step 400, the unit 22 or a logic unit integrated into the detector 504 accesses the data set D1 in the memory 504M or in an equivalent memory of the unit 22 in order to perform the comparison of the spectrums S1 and S2.

During a following step 500 of the calibration process, the corrected second spectrum S2' is entered into the memory 504M of the detector 504, in the form of a second data set D2, to constitute a reference spectrum for the sensor 50, to which reference spectrum a comparison is made of the peaks detected by the detector 504 during the subsequent use of the sensor 50, as emerges from the following explanations.

Alternatively, the data set D2 can be stored in a memory of the unit 22.

According to one advantageous aspect of the invention, the first spectrum S1 can be established by taking account of the fact that the nature of the component material of the anode of the x-ray source 502 influences the energy levels that correspond to the most pronounced peaks in the second collected spectrum S2. Indeed, two characteristic energy levels $E_{10}$ and $E_{11}$ generally correspond to particular peaks in the second spectrum S2, these energy levels being known for the materials most commonly used to make up the anode of an x-ray source. Thus, for a gold anode, peaks are observed for the energy levels of 9.71 and 11.44 keV. For a silver anode, peaks are observed for energy levels of 2.98 keV and 3.15 keV. For a tungsten anode, peaks are observed for energy levels of 8.40 keV and 9.60 keV. For a rhodium anode, peaks are observed for energy levels of 2.70 keV and 2.83 keV.

Since the secondary x-radiation comes from the primary x-radiation, this secondary radiation, as detected by the detector 504 of the sensor 50, normally comprises peaks for the energy levels $E_{10}$ and $E_{11}$ of the material of the anode.

The component material of the anode of the radiation source X502 being known, the energy levels $E_{10}$ and $E_{11}$ are known and can be incorporated into the data set D1 of the first spectrum S1 to be used to align or "recalibrate" the second spectrum S2 on the first spectrum S1 during step 400. In this case, the first spectrum S1, as it is stored in the memory 504M to be used in step 400, also comprises the energy levels $E_{10}$ and $E_{11}$.

Figure 7:
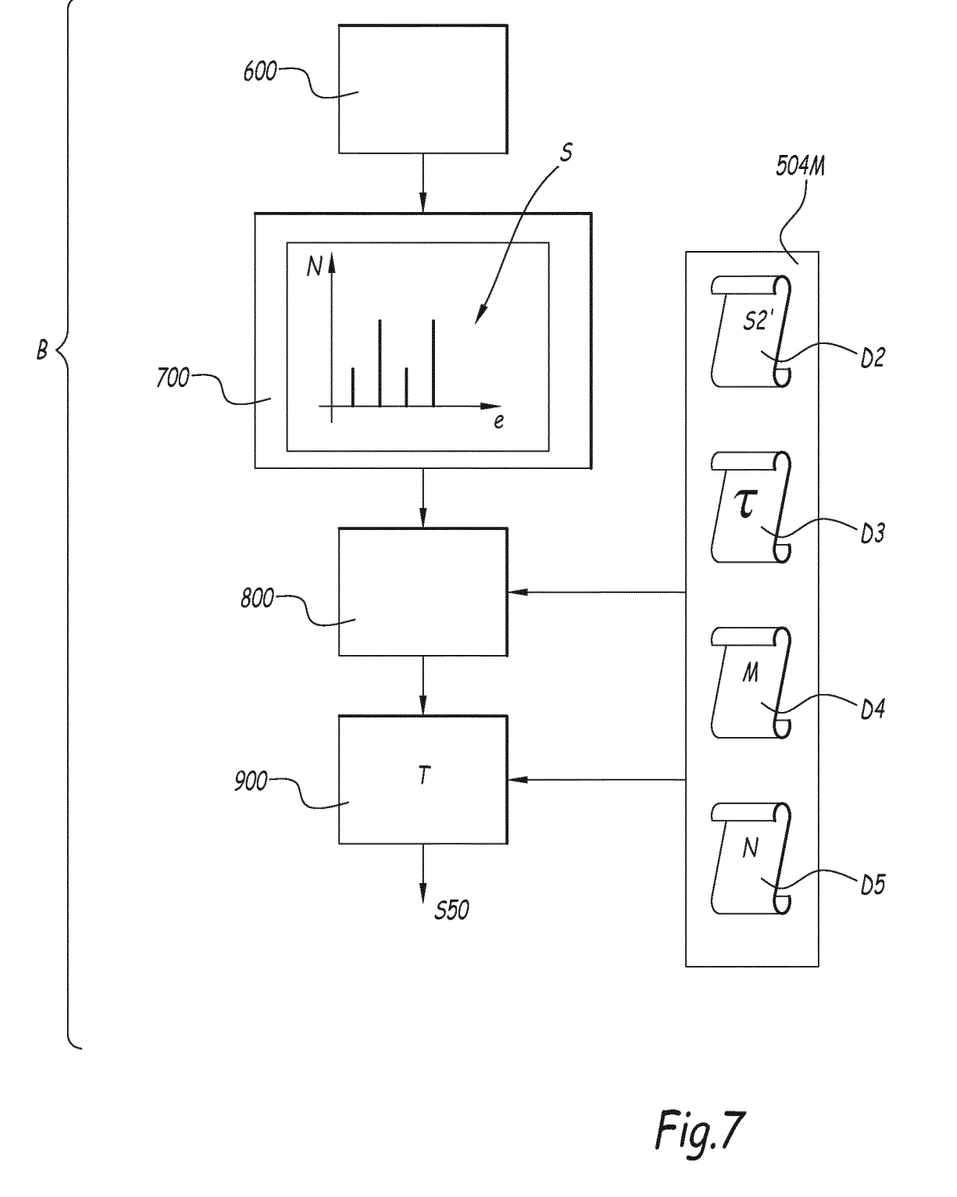
FIG. 7 is a block diagram of a method for online monitoring of the changes to the iron content of a liquid body, also according to the invention.

As shown in FIG. 7, when the sensor 50 is used for the online monitoring of the changes of the iron content of lubricant circulating in the equipment M, the sensor is started during a step 600 and the detector 504 acquires, during a step 700, a spectrum S, with an operation similar to that implemented during step 300, the volume V508 then being filled with lubricant to be analyzed, during flow.

During a subsequent step 800, the acquired spectrum S is compared to the reference spectrum S2' to identify the number of peaks corresponding to an energy level equal to about 6.4 keV and/or 7.06 keV, i.e., equal to 6.4 keV and/or 7.06 keV, plus or minus 5%.

The number of blows corresponding to the energy level of 6.4 keV representative of the iron being known, it is possible to compare it, during a step 900, to the number of peaks detected for reference samples, during manipulations done in the laboratory where each dissolved iron and particulate iron content was associated with a number of blows, i.e., a peak height, for the value of 6.4 keV.

The number of peaks detected for the reference samples based on the dissolved iron and particulate iron content $\tau$ was stored beforehand, in the form of a data set D3, within the memory 504M. The information of the data set D3 is provided to a calculator of the detector 504 during step 900, which allows the calculator to identify the iron content to which the detected peak corresponds for the energy level of 6.4 keV. This value of the iron content T can then be incorporated into the signal S50.

In practice, the automated method for online monitoring of the iron content of a liquid body comprises two main parts, namely part A, shown in FIG. 6, which corresponds to the process for calibrating the sensor, and part B, shown in FIG. 7, which corresponds to the actual measurement of the iron content of the sample, once the sensor 50 has been calibrated beforehand. Part B can only be done precisely once part A has been carried out.

The fact that the monitoring method is based on an x-ray fluorescence detection within the sensor 50 means that it is a non-destructive method, such that the analyzed oil can be reinjected toward the machine M.

Parts A and B of the method can be implemented automatically. In particular, the calibration process can be implemented automatically, before each measurement or series of measurements of the iron content of a lubricant within the installation 2. Alternatively, this process can be implemented at regular intervals, for example once per day, always automatically.

To carry out steps 300 to 900, the volume V508 of the casing 508 can be supplied successively with air and lubricant to be analyzed, from the tank 26, subject to appropriate steering of the valves 32, 36, 40 and 44.

The intensity and position of the peaks within the spectrum S depends on the matrix of material surrounding the iron atoms within the sample present in the volume V508 during step 700. In other words, interactions take place between the iron atoms present in the sample and their environment. This phenomenon is known as "matrix effect". In particular, the other atoms present in the lubricant absorb electrons emitted by the iron atoms, which results in attenuating the secondary x-radiation. Furthermore, the atoms that absorb the electrons in turn re-emit electrons that may excite the iron atoms, which participates in amplifying the secondary x-radiation. Furthermore, the lubricant atoms that surround the iron atoms also tend to absorb the primary fluorescence radiation from the source 502.

During step 800 identified above, this matrix effect is taken into account by correcting the height of the peak corresponding to an energy of about 6.4 keV.

This correction is made based on a model MP previously stored in the memory 504M in the form of a data set D4. This model may be a semi-empirical model using several reference samples, the concentrations of which are similar to the unknown samples to be analyzed, as considered by N. Broil in "Fluorescence X: de la découverte des rayons de Rontgen aux identités de Tertian" [X-ray Fluorescence: from the discovery of Rontgen rays to Tertian identities] J. Phys. IV, Vol. 06, No. C4, pp C4-583-C4-596, 1996. The model MP may also be a theoretical model based on the equation of the fundamental parameters of the samples used, as considered by B. Beckhoff, Habil. B. Kanngiesser, N. Langhoff, R. Weddell and H Wolff in "Handbook of practical X-ray fluorescence analysis", Berlin, Heidelberg Springer, 2006.

Furthermore, the method for the online monitoring of changes in the iron content of the oil may also account for the fact that the lubricants of equipment such as wind turbines most commonly used are fairly charged with calcium, which results in disrupting the detection of the secondary x-radiation from iron. It is therefore possible to establish a model NP that correlates a spectrum established for a given iron content in the absence of calcium and a spectrum established under the same conditions in the presence of calcium, in one or several concentration(s) typically encountered in an industrial equipment lubricant. In particular, calcium corresponds to an energy level in the spectrum equal to about 3 keV. The model NP is stored in the memory 504M in the form of a data set D5 and may be used during step 800 or during step 900 to correct either the spectrum S or the calculation of the iron content. The model NP may be established theoretically or experimentally.

Alternatively, the data sets D4 and D5 are stored in a memory of the electronic control unit 22.

The installation 2 also comprises a first level sensor 54 and a second level sensor 56 that respectively make it possible to detect when the quantity of oil in the tank 26 reaches a first level N1 or a second level N2. The electrical output signals S54 and S56 of the sensors 54 and 56 are delivered to the unit 22.

Alternatively, the sensors 54 and 56 can be replaced by a single sensor, such as a pressure sensor, that makes it possible to detect when the oil reaches each of the two levels N1 and N2 in the tank 26.

FIGS. 8 to 11 schematically illustrate the successive steps of an automated process carried out using the installation 2 of FIG. 1. This process is automated inasmuch as it can be implemented, partially or preferably totally, without human intervention, under the control of the unit 22. The same is true for the process explained below regarding the second embodiment of the invention.

By default, and outside withdrawal phases, the oil leaving the equipment M flows in the pipe 4, in the direction of arrow F1 in FIG. 1, from the equipment M toward the oil pan 6, without being retained by the valve 20, which is in the open or on configuration, while the other valves are closed.

When it is appropriate to determine the iron content of the oil leaving the equipment M, the unit 22 orders the valve 20 to close, such that a retention is created in the pipe 4 where a quantity of oil, i.e., lubricant, accumulates, as shown by the gray part L in FIG. 2.

Figure 8:
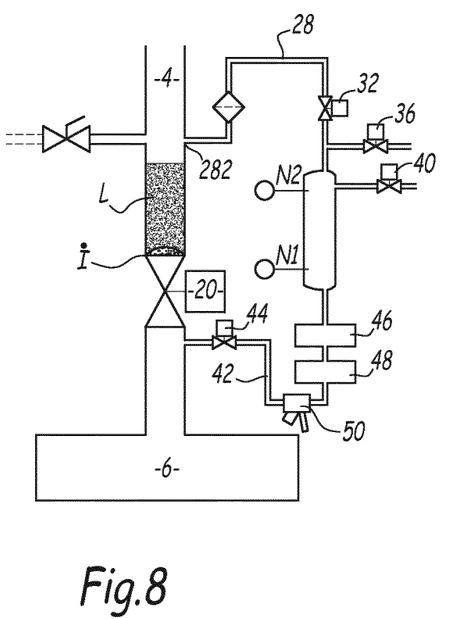
FIG. 8 is a smaller-scale schematic illustration of the fluid part of the installation of FIG. 1 in a first usage configuration.
Figure 9:
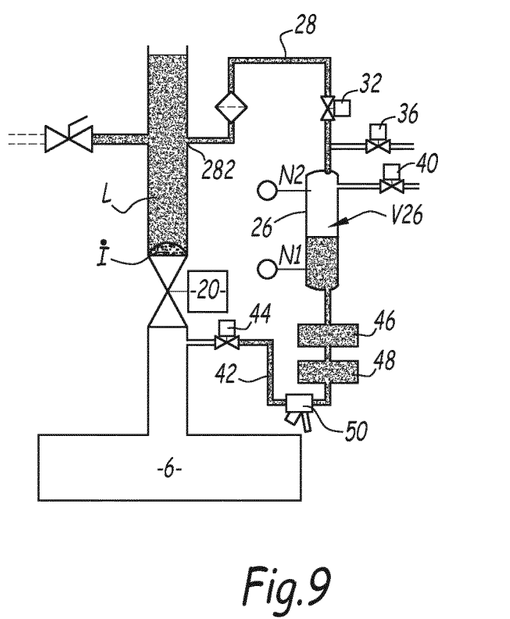
FIGS. 9 to 11 are views similar to FIG. 8 when the installation is in a second, third and fourth usage configuration.

In the configuration of FIG. 8, the pipe 4 serves as a decanting column and impurities I accumulate near the valve 20, inside the pipe 4 and in the lower part of the quantity of lubricant L.

In this first step shown by the configuration of FIG. 8, the valves 32 and 40 are open, while the valves 36 and 44 are closed.

When the level of lubricant L in the pipe or column 4 reaches the mouth 282, oil begins to flow through the first bypass line 28, more particularly through the filter 30 and the valve 32, to the inner volume V26 of the tank 26 in which the oil flows by gravity. Indeed, the outlet 284 of the first line 28 is situated in the upper part of the tank 26 and the oil can flow along the wall of the tank 26. Since the valve 44 is closed, the oil gradually fills the part of the second discharge line 42 situated upstream from the valve 44, including the inner volumes of the sensors 46 and 48, then the inner volume V26, driving the air toward the atmosphere, through the valve 40. This step corresponds to the configuration shown in FIG. 9.

Figure 10:
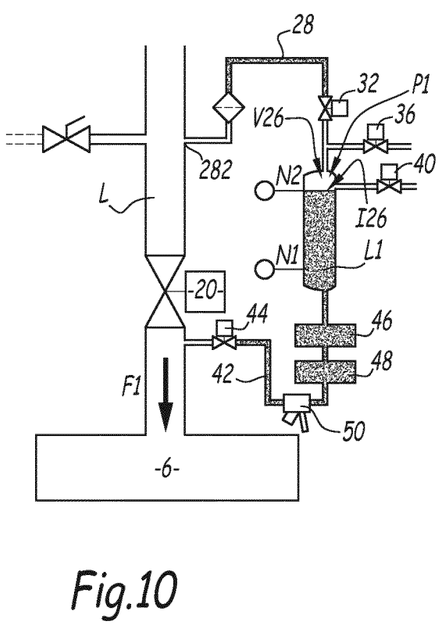

When the sensor 56 detects that the oil level N2 inside the tank 26 has been reached, the unit 22 switches the installation 2 toward a new configuration shown in FIG. 10, in which the valve 20 enters the open configuration, which makes it possible to empty the decanting column by steering the remainder of the quantity L of lubricant present upstream from the valve 20 as well as the impurities I toward the oil pan 6. The flow in the direction of arrow F1 therefore continuous to the pan 6. Furthermore, the valves 32 and 40 are closed and the valve 36 is open, which makes it possible to place the part of the volume V26 that is not occupied by the lubricant, i.e., the part of the volume V26 situated above the level N2, under an air pressure P1 equal that of the air source 12, which, in the example, is equal to 7 absolute bars.

Figure 11:
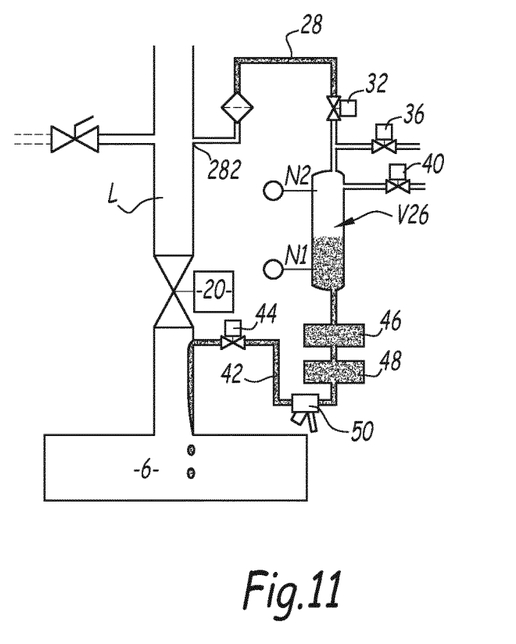

Once this is done, the unit 22 causes the installation 2 to go to a following step, shown by the configuration of FIG. 11, where the valve 44 is open, the other valves retaining their state of the configuration of FIG. 4. In this case, the pressure P1 of the air in the upper part of the volume V26 results in pushing the oil in the second discharge line 42 through the sensors 46, 48 and 50, which allows these sensors to provide the unit 22 with signals S46, S48 and S50, respectively, representing parameters that they have detected.

If applicable, the signals S46, S48 and S50 can be processed in the unit 22 in order to determine the values of the monitored parameters, in particular by comparison with known values for reference lubricants.

The signals S46, S48 and S50, or signals extrapolated from these signals, can be provided outside the installation 2 in the form of a conjugated signal S2, usable by a central control unit of the equipment M.

In practice, the passage section of the iron content sensor 50 is around 70 mm$^2$. It may reach up to 200 mm$^2$. In any case, this passage section should be able to be supplied with a sufficient flow rate, for a sufficient duration to take the measurement of the overall iron content. Alternatively, the same is true for the base number sensor 48. Building the installation with the tank 26 makes it possible to create a tank forming an oil "buffer", in the form of the quantity of oil L1 contained in the tank 26 in the configuration of FIG. 4. Part of this oil reserve L1 can be poured, continuously or sequentially, in the second discharge line 42 in order for the sensors 48 and 50 to have a sufficient quantity of oil to analyze.

From the configuration of FIG. 11, it is possible, in a subsequent step, to continue emptying the tank 26 and all of the second discharge line 42 by keeping the valve 44 open and continuing to inject compressed air through the valve 36.

Alternatively, it is possible to stop emptying the tank 26 when the oil level reaches the level N1, so as to continuously keep a quantity L2 of oil in the second discharge line 42, in particular in the sensors 46, 48 and 50 whose active parts in contact with the oil do not risk drying. This in particular prevents traces of oil from being deposited on the wall 510 of the sensor 50. If this second approach is selected, a certain quantity of oil must be used during a close measurement, to clean the second discharge line 42 beforehand and not disrupt the next measurement.

According to one alternative of the invention that is not shown, the installation 2 can be modified so that the first and second lines 28 and 42 come together at a T branch arranged in the lower part of the tank 26. In this case, the tank 26 is filled from the bottom. Furthermore, the level sensors 54 and 56 can be replaced by a sensor for the internal pressure of the tank 26.

According to another alternative of the invention that is not shown, several pipes comparable to the pipe 4 are used, each of them being provided to collect oil from part of the equipment M. In this case, each of said pipes is equipped with a valve comparable to the valve 20, which allows them to supply, in parallel, a shared buffer tank comparable to the tank 26. Like in the first embodiment, a sensor, identical to the sensor 50, is arranged in a pipe for discharging lubricant from this buffer tank.

The invention is described above in the case where the sensor 50 is used to determine the iron content of a lubricant. It is, however, applicable for determining the content of a lubricant in another predetermined chemical element, for example calcium, sulfur, vanadium, chromium, molybdenum, copper, silver, tin, aluminum, nickel, zinc, lead or phosphorus. In all cases, the component material of the casing is suitable for the chemical element in question, as well as the energy level(s) used in step 800. "Suitable for the chemical element" means that the component material of the casing does not comprise said chemical element, which prevents a disruption of the measurement.

The invention is described above in the case of its use for equipment M of the wind turbine type. It is, however, applicable to other equipment, for example an auxiliary device or accessory of a ship, such as a transmission, in particular a marine or wind turbine transmission, or in a refinery.

In the preceding, the words "oil" and "lubricant" are used interchangeably, since within the meaning of the invention, an oil is a lubricant. The invention is, however, applicable to other liquid bodies, such as heavy or light fuel oil, before or after refining to control the level of sulfurous elements. The invention is applicable to oil for transmissions, oils for gears, oils for compressors, hydraulic oils, turbine oils or oils for centrifuges. The invention is also applicable to the continuous monitoring of water pollution by metal elements such as lead, and more generally, any liquid body.

In the preceding, the expressions "iron content", "overall iron content" and "dissolved and/or particulate iron content" are used indifferently, as well as the expressions "content in predetermined chemical element" and "overall content in predetermined chemical element".

The calibration process of the invention can be implemented for a sensor 50 intended to be used in an environment other than the installation 2. In this case, during step 300 for establishing the second secondary radiation spectrum S2, it is possible for the internal volume V508 of the casing 508 to be filled with a gas other than air.

The sensor 50 is in particular intended to implement the calibration process and the monitoring method mentioned above. It may also be used in another context.

The features of the embodiments and alternatives considered above may be combined to generate new embodiments of the invention.

The invention claimed is:

1. A process for calibrating a sensor for determining the content of a predetermined chemical element in a liquid body, said sensor using x-ray fluorescence technology and comprising an x-ray source, an x-ray detector and a cell intended to contain a sample of liquid body to be analyzed, said cell in turn including a casing that defines an internal volume for receiving the sample, wherein the process includes at least the following steps:

a) establishing a first secondary x-ray spectrum comprising energy levels corresponding to the components of the material of the casing;
   b) operating the sensor, while the internal volume of the casing does not contain a sample of the liquid body and establishing a second secondary x-ray spectrum;
   c) modifying the second spectrum, using the first spectrum as a base spectrum, for aligning the notable energy levels of the second spectrum on those of the first spectrum; and
   d) recording the modified second spectrum as reference spectrum for the sensor.

2. The process according to claim 1, wherein, during step b), the internal volume of the casing exclusively contains a gas or a gaseous mixture, inert with respect to the x-rays, in particular air.

3. The process according to claim 1, wherein the casing is made from metal and the notable energy levels of the first reference spectrum comprise energy levels of metals making up the box.

4. The process according to claim 3, wherein the predetermined chemical element whereof one wishes to determine the content is iron and the metals whose energy levels make up the first spectrum do not comprise iron.

5. The process according to claim 1, wherein the first spectrum also comprises at least one energy level corresponding to the material of an anode of the x-ray source.

6. An automated method for online monitoring of the changes in content of a predetermined chemical element of a liquid body circulating in a piece of equipment using an installation comprising a sensor for the content of a predetermined chemical element of said liquid body, said sensor using x-ray fluorescence technology and comprising an x-ray source, an x-ray detector and a cell intended to contain a sample of liquid body to be analyzed and including a casing defining an internal volume for receiving said sample, wherein the method comprises the prior implementation of a process for calibrating the sensor according to claim 1, as well as at least one series of steps consisting of determining, owing to the sensor previously calibrated, the content in predetermined chemical element of a sample of liquid body present or circulating in the internal volume of the casing.

7. The method according to claim 6, wherein the predetermined chemical element is iron, or another chemical element, and the series of steps comprises detecting peaks for an energy level equal to about 6.4 keV and/or 7.06 keV in a secondary x-ray radiation spectrum emitted by the liquid body for iron, or specific rays for the other predetermined chemical element.

8. The method according to claim 6, wherein during the series of steps, a potential matrix effect is taken into account within the sample by applying a correction on the energy levels detected by the sensor, based on a predetermined interaction model between the components of the sample and/or the components of the casing.

9. The method according to claim 8, characterized in that during the series of correction steps, the calcium concentration of the sample is further taken into account by applying a correction on the energy levels detected by the sensor, based on a predetermined model.

10. A sensor for determining, using x-ray fluorescence technology, the overall content, in predetermined chemical element, of a liquid body, said sensor in particular being intended to implement a calibration process according to claim 1 and comprising an x-ray source, an x-ray detector and a cell intended to contain a sample of the liquid body to be analyzed, this cell being equipped with a wall forming a window for the passage of the rays coming from the source or going toward the x-ray detector and the wall being made from polyethylene terephthalate.

11. The sensor according to claim 10, wherein the cell comprises a casing made from metal, or metal alloy, on which the wall is attached, and in that wherein, preferably, the cell comprises a hollow housing for receiving the wall and a threaded washer for immobilizing the wall in the hollow housing.

12. The sensor according to claim 10, wherein the membrane has a curved shape, with its concavity turned toward an inner volume of a housing of the cell.

13. The sensor according to claim 10, wherein the x-ray source, the x-ray detector and the cell are mounted on a common support.

14. The sensor according to claim 10, wherein the wall has a thickness that is
  less than or equal to 200 μm, preferably less than or equal to 150 μm, still more preferably about 125 μm, or
  less than or equal to 500 μm, preferably about 250 μm, and
  greater than or equal to 75 μm.

15. The sensor according to claim 10, wherein it is compatible with a static or dynamic determination of the content of the liquid body in predetermined chemical element.

* * * * *